United States Patent [19]

Guthauser

[11] Patent Number: 5,162,378
[45] Date of Patent: Nov. 10, 1992

[54] SILICONE CONTAINING WATER-IN-OIL MICROEMULSIONS HAVING INCREASED SALT CONTENT

[75] Inventor: Bernadette Guthauser, North Bergen, N.J.

[73] Assignee: Revlon Consumer Products Corporation, New York, N.Y.

[21] Appl. No.: 511,704

[22] Filed: Apr. 20, 1990

[51] Int. Cl.$^5$ .................. A01N 25/04; A61K 7/107; A61K 7/32; B01J 13/00
[52] U.S. Cl. ...................... 514/785; 424/65; 424/66; 424/67; 424/68; 424/401; 252/309; 514/938
[58] Field of Search ............. 252/309; 514/937, 938, 514/63, 785; 424/401, 67, 65, 66, 68

[56] References Cited

U.S. PATENT DOCUMENTS

| | | | |
|---|---|---|---|
| 4,122,029 | 10/1978 | Gee et al. | 252/309 |
| 4,268,499 | 5/1981 | Keil | 424/66 |
| 4,311,695 | 1/1982 | Starch | 514/938 X |
| 4,362,747 | 12/1982 | Coursen | 424/358 |
| 4,532,132 | 7/1985 | Keil | 514/772 |
| 4,563,346 | 1/1986 | Deckner | 424/59 |
| 4,613,592 | 9/1986 | Benzoni | 514/63 |
| 4,673,570 | 6/1987 | Soldati | 424/66 |
| 4,698,178 | 10/1987 | Huttinger | 252/309 |
| 4,720,353 | 1/1988 | Bell | 252/309 |
| 4,772,592 | 9/1988 | Benzoni | 514/63 |
| 4,782,095 | 11/1988 | Gum | 514/937 |
| 4,797,272 | 1/1989 | Linn et al. | 514/937 X |
| 4,822,602 | 4/1989 | Sabatelli | 424/65 |
| 4,900,542 | 2/1990 | Parrotta | 424/66 |
| 5,008,103 | 4/1991 | Raleigh et al. | 514/938 X |
| 5,077,040 | 12/1991 | Bergmann et al. | 424/70 |

OTHER PUBLICATIONS

*CTFE International Cosmetic Ingredient Dictionary*, 4th ed., (Cosmetic, Toiletry, and Fragrance Ass., Wash., DC, 1991) pp. 94, 161, 162.

Hameyer, et al., Manufacturing Chemist, Jan. 1990, p. 21.

*Primary Examiner*—Robert L. Stoll
*Assistant Examiner*—Daniel S. Metzmaier
*Attorney, Agent, or Firm*—Julie Blackburn

[57] ABSTRACT

A water in oil microemulsion comprising the following essential constituents:
a) cetyl dimethicone copolyol,
b) water,
c) silicone,
d) alcohol, and
e) about 5–40% by weight of one or more salts.

The inventive compositions are useful in personal care products including moisturizing and antiperspirant compositions.

4 Claims, No Drawings

SILICONE CONTAINING WATER-IN-OIL MICROEMULSIONS HAVING INCREASED SALT CONTENT

TECHNICAL FIELD

The invention is directed to silicone containing water in oil microemulsions which comprise cetyl dimethicone copolyol, water, silicone, alcohol, and an increased amount of one or more of an inorganic salt, organic salt, or polar compound. These compositions are useful in the preparation of moisturizers, anti-perspirants, sunscreens, and other cosmetic preparations.

BACKGROUND OF THE INVENTION

Various products and formulations have been used throughout the years for the treatment of or use on human skin in the attempt to keep the skin in a smooth supple condition or to prevent some condition or unpleasant characteristic. Many of the formulations used to make personal care products are in the form of emulsions. The preparation of aesthetically acceptable emulsion products involves attention to properties such as tackiness, greasiness, lubricity, feel, and safety. Silicones are most desirable as components of water/oil emulsions used to make personal care products because they impart a velvety smooth quality, adhere well to the skin, spread easily, and dry quickly without a heavy or greasy feel. However, until just recently it has been very difficult to use silicone in appreciable amounts in water in oil emulsions since the resulting emulsions are unstable and usually break within hours or days. This problem was partially solved with the discovery of a group of polyoxyalkylene-polysiloxane copolymers which are described in U.S. Pat. No. 4,698,178. These compounds, sold by Goldschmidt Corporation under the trade name ABIL B 9806, ABIL WE-09, ABIL B 9?08, or ABIL WS-08, function as emulsifiers in silicone containing water in oil emulsions. The use of these compounds results in emulsions which have increased stability and do not readily disintegrate into separate water and oil phases. The level of emulsifier is directly proportional to the dispersion of the water phase in the oil phase i.e. the greater the level of emulsifier the greater the number of water droplets dispersed in the oil phase. A water in oil microemulsion results when the water is dispersed throughout the oil phase in the form of "micro" droplets so that the droplet size is smaller than the wavelength of light. Microemulsions are very desirable in personal care products because they are excellent vehicles for enabling penetration into the skin of active ingredients which would not normally penetrate the stratum corneum. Moreover, clear microemulsions are desired since an opaque, pearlescent, or cloudy appearance is not always pleasing particularly if the product is used as a base for personal care items where a very fresh, clean and clear look is desired, such as sunscreen products, skin hydrating moisturizers or antiperspirants. As a rule, to achieve a clear water in oil microemulsion containing silicones the addition of very high levels of emulsifiers is required, in the order of 20% or more. This is not desirable since organo silicone emulsifiers are very expensive. At the high levels required to achieve a microemulsion these emulsifiers may cause irritation to the skin as well as resulting in a composition which is very tacky when applied to the skin even though organo functional polysiloxane type emulsifiers exhibit less tackiness than the conventional water in oil emulsifiers. However, if the level of emulsifier is decreased to too low a level to minimize expense, a loss of stability and aesthetic appearance results, the composition becomes cloudy and opaque, and the viscosity of the composition in turn decreases resulting in an emulsion with less than desirable consistency.

Microemulsions of a high consistency are difficult to formulate. The thickening agents which are used to control the rheological properties of conventional emulsions will more than likely prevent the formation of microemulsions. It is known that the addition of salt to water in oil emulsions based upon organo functional silicone emulsifiers increases their stability but the amounts recommended by the prior art are quite small, generally 1 to 2 percent. However, these small levels are sufficient only to enhance the viscosity and stability of microemulsions of low consistency. Thus, to date most microemulsions exist in the form of lotions since cream type microemulsions do not have the luxuriant "feel" and safety required for marketable cosmetic preparations.

There is therefore a need for silicone containing water in oil microemulsions which are not opaque or cloudy, have a pleasing appearance and firm consistency, and are not tacky, irritating to the skin or expensive.

SUMMARY OF THE INVENTION

The invention is directed to water in oil emulsions comprising the following essential constituents:
(a) cetyl dimethicone copolyol,
(b) water,
(c) silicone,
(d) organic alcohol, and
(e) 5–40% by weight of one or more salts.

The invention is also directed to a variety of personal care products containing the microemulsion of the invention.

DETAILED DESCRIPTION

The invention is based upon the discovery that adding alcohol as well as increased levels of one or more salts to a water in oil emulsion comprised of cetyl dimethicone copolyol, silicone, and water results in a clear microemulsion which is stable, has excellent viscosity and consistency, and is not tacky or irritating to the skin. The addition of alcohol and an increased level of salt imparts a multiplicity of advantages which were not expected. For example, a high level of salt permits the level of emulsifier to be reduced without affecting the stability of the composition. Unexpectedly this increases not only the viscosity of the microemulsion but adds clarity as well. Thus these emulsions are less expensive to make and the tackiness found in preparations containing a high level of cetyl dimethicone copolyol and other co-emulsifiers is eliminated. The high level of salt also yields an emulsion with excellent viscosity, consistency, and a high relative level of continuous phase to assure smooth, easy spreading on the skin. In prior art formulations viscosity was controlled by the addition of parraffin waxes, fatty acid derivatives with long alkyl chains, or substances of similar constituency in their molecular backbones. Further, the high salt concentration enables a clear microemulsion to which may be added ingredients which are very desirable in moisturizing compositions including humectants such as urea. Urea is a very desirable component of moisturing compositions because of its proven hydrating effects and its healing effect on minor cuts. However, its use has been somewhat restricted because it is unstable in anionic cosmetic preparations. In general urea destabilizes most emulsification systems due to its high polarity. Thus very high levels of emulsifiers are needed to ensure stability which in turn cause "drag" and "tack" when the composition is applied.

The emulsifier which is used in this invention has the CTFA name cetyl dimethicone copolyol. It is available under the product name ABIL B 9806, ABIL WE-09, ABIL B 9808 or ABIL WS-08 from its supplier the Goldschmidt Chemical Corporation, Hopewell, Va. The silicone used may be dimethicone, methicone, cyclomethicone, phenyl dimethicone, hexamethyldisiloxane, trimethylsiloxysilicate, or stearoxy-trimethylsilane. Dimethicone is a polydimethylsiloxane having a molecular weight of about 500-26,000. Methicone means a polymethyl hydrogen siloxane of molecular weight about 500-23,000. Cyclomethicone means a cyclic tetramer of dimethylsiloxane of molecular weight about 296 or the cyclic pentamer of dimethyl siloxane having a molecular weight of approximately 370.

The term "salt" means either an inorganic salt or an organic salt.

A variety of inorganic salts are acceptable including alkali metal and alkaline earth metal halides, sulphates, nitrates, and carbonates or bicarbonates for example, magnesium sulfate, magnesium chloride, sodium thiosulfate, aluminum chloride, sodium chloride, aluminum chlorohydrate, aluminum zirconium tetrachlorohydrex gly, aluminum zirconium trichloro-, tetrachloro-, or octachlorohydrate, sodium acetate, sodium citrate, sodium phosphate, calcium chloride, ammonium carbonate, sodium dehydroacetate and the like.

Suitable organic salts are sodium aluminum lactate, sodium butoxyethoxy acetate, sodium caprylate, sodium citrate, sodium lactate, sodium dihydroxyglycinate, sodium gluconate, sodium glutamate, sodium hydroxymethane sulfonate, sodium oxalate, sodium phenate, sodium propionate, sodium saccharine, sodium salicylate, sodium sarcosinate, sodium toluene sulfonate, magnesium aspartate, calcium propionate, calcium saccharin, calcium D-sacharate, calcium thioglycolate, aluminum caprylate, aluminum citrate, aluminum diacetate, aluminum glycinate, aluminum lactate, aluminum methionate, aluminum phenosulfonate, potassium aspartate, potassium biphthalate, potassium bitartrate potassium glycosulfate, potassium sorbate, potassium thioglycolate, potassium toluenesulfonate, potassium troclosene, or magnesium lactate.

The organic alcohol component is a straight or branched chain $C_{1-6}$ organic alcohol. Preferred however, are straight or branched chain $C_{1-6}$ organic alcohols such as isopropanol, ethanol, methanol, propanol, butanol, glycols such as ethylene glycol and propylene glycol, glycerine, sorbitol, SD-40 alcohol, etc.

The general ranges of the essential constituents of the composition are about 1-35% cetyl dimethicone copolyol, about 5-70% water, about 5-80% silicone, about 1-50% alcohol, and about 5-40% of one or more salts.

The preferred ranges of essential constituents are about 8-20% cetyl dimethicone copolyol, 20-40% water, 10-35% silicone, 8-25% of one or more salts and about 5-15% alcohol. This is the "core" composition which may be used to make a variety of personal care products.

A great variety of optional ingredients may be added to the core composition such as co-emulsifiers, thickeners, preservatives, humectants, masking agents, coloring agents, U.V. absorbers, vitamins, hormones, plant extracts, emollients, solvents, moisturizers, anti-oxidants and so forth. Examples of these optional additives include but are not limited to the following.

Emollients

| | |
|---|---|
| Stearyl alcohol | Glyceryl monostearate |
| Glyceryl monoricinoleate | Polyethylene glycols |
| Glyceryl monostearate | Oleic acid |
| Sulphated tallow | Triethylene glycol |
| Propylene glycol | Lanolin |
| Mink oil | Castor oil |
| Cetyl alcohol | Acetylated lanolin alcohols |
| Stearyl stearate | Acetylated lanolin |
| Isopropyl isostearate | Petrolatum |
| Dimethyl brassylate | Isopropyl ester of lanolin |
| Stearic acid | fatty acids |
| Isobutyl palmitate | Mineral oils |
| Isocetyl stearate | Butyl myristate |
| Oleyl alcohol | Isostearic acid |
| Isopropyl laurate | Palmitic acid |
| Sorbitan Stearate | PEG-23 oleyl ether |
| Hydrogenated Castor Oil | Olelyl Oleate |
| Hydrogenated soy glycerides | Isopropyl linoleate |
| Hexyl laurate | Cetyl lactate |
| Decyl oleate | Lauryl lactate |
| Diisopropyl adipate | Myristyl lactate |
| n-dibutyl sebacate | Quaternised hydroxy alkyl |
| Diisopropyl sebacate | aminogluconate |
| 2-ethyl hexyl palmitate | Vegetable Oils |
| Isononyl isononanoate | Isodecyl oleate |
| Isodecyl isononanoate | Isostearyl neopentanoate |
| Isotridecyl isononanoate | Myristyl myristate |
| 2-ethyl hexyl palmitate | Oleyl ethoxy myristate |
| 2-ethyl hexyl stearate | Diglycol stearate |
| Di-(2-ethyl hexyl) adipate | Ethylene glycol monostearate |
| Di-(2-ethyl hexyl) succinate | Myristyl stearate |
| Isopropyl myristate | Isopropyl lanolate |
| Isopropyl palmitate | Parraffin waxes |
| Isopropyl stearate | Glycyrrhizic acid |
| Octacosanol | Hydrocyethyl stearate amide |
| Butyl stearate | |

Co-emulsifiers/Solvents

| | |
|---|---|
| Ethyl alcohol | Methoxy PEG-22 |
| 2-ethylhexanol | dodecyl-glycol copolymer |
| Ethylene carbonate | PEG-30 Glyceryl monoacetate |
| Propylene carbonate | sorbitol |
| N-methyl glucamine | PEG-3 oleyl ether phosphate |
| Linear ethoxylated polymer of methanol | PEG-(2-5) oleyl ether |
| | PPG-(2-5) lanolate |
| Ethylene glycol monoethyl ether | PPG-(2-8) isostearate |
| Diethylene glycol monoethyl ether | Propylene glycol (2) methyl ether |
| Diethylene glycol monoethyl ether | PPG-(2-3) methyl ether |
| | PPG-14 butyl ether |
| Propoxylated oleyl alcohol | Ethoxylated (2-20 moles) |
| Butyl stearate | glucose |
| Butyl myristate | Propoxylated (2-20 moles) |
| Isopropyl alcohol | glucose |
| SD-40 alcohol | PPG-15 Stearyl ether |
| Mineral spirits | PPG-(5-20) methyl glucose |
| PPG (2-8) myristyl ether | ether |
| PPG (2-8) lauryl ether | |
| PPG (2-10) cetyl ether | |
| PEG-6 diisopropyl adipate | |

Humectants

Urea
Glycerin
Sorbitol
Sodium 2-pyrrolidone-5-carboxylate
Soluble collagen
Dibutyl phthalate
Gelatin
Polyglycerogen
Propylene glycol
Butylene glycol
Ethyl hexanediol
$C_{1-10}$ polyethylene glycols Hyaluronic acid
Lactic acid
Sodium pyrrolidone carboxylate
Sodium lactate
Orotic acid Antiseptics/Preservatives/Antioxidants/Chelating Agents Cetyl pyridinium chloride | Paraformaldehyde
Tribromosalicylanilide | Thimerosol
Benzalkonium chloride | Dodecyl gallate
Dehydroacetic acid | Hydroquinone
Methyl paraben | Phenol
Propyl paraben | Sodium pyrithione
Sodium dehydroacetate | Stearalkonium chloride
Quaternium-15 | Tetrapotassium pyrophosphate
EDTA Benzyl alcohol | Benzoxiquine
Chlorobutanol | Chlorobutanol
Dichlorobenzyl alcohol | Quaterniuim-11
Phenethyl alcohol | U.V. absorber-1
Phenoxyethanol | Disodium phosphate
Propylene glycol | Trisodium HEDTA
Chloroacetamide | Benzethonium chloride
Imidazolidinyl urea | Sodium methyl paraben
Butyl paraben | DMHF
Butylated Hydroxy Anisol | MDM hydantoin
Ethyl paraben | O-phenylphenol
5-chloro-2-methyl-4- | Chlorhexidine digluconate
isothiazolin-3-one | Myristalkonium chloride
2-methyl-4-isothiazol-3-one | Ascorbyl palmitate
formaldehyde | Isopropyl paraben
Butylated Hydroxy Toluene | Quaternium-15
DMDM hydantoin | Benzylparaben
2-bromo-2-nitropropane-1,3-diol | Phenethyl alcohol
Sorbic acid | Phosphoric acid
Citric acid | Sodium O-phenyl phenate
Triclosan | Chlorhexidine dihydrochloride
Diazolidinyl urea | Phenoxyisopropanol
Benzoic acid | Resorcinol
Propyl gallate | Dichlorophen, sodium salt
Sodium benzoate | T-butyl hydroquinone
Potassium sorbate | Dichlorophen
Chloroxylenol | Methylbenzethonium chloride
5-bromo-5-nitro-1,3-dioxane | Chloroacetamide
Glutaral | Phenylmercuric acetate
Tocopherol | Ascorbic acid
Zinc pyrithone | Benzyl benzoate
Sodium borate | Hydantoin
Boric acid | Sodium sulfite
Isobutyl paraben | Sodium bisulfite
2-(hydroxymethylamine)-ethanol | Iodine U.V. Absorbers 2-hydroxy-4-methoxybenzophenone
Octyl dimethyl p-aminobenzoic acid
Digalloyl trioleate
2,2-dihydroxy-4-methoxy benzophenone
Ethyl 4-[bis(hydroxypropyl)] aminobenzoate
2-ethylhexyl 2-cyano-3,3-diphenylacrylate
Ethyl hexyl p-methoxy cinnamate
2-ethylhexyl salicylate
Menthyl anthranilate
p-dimethyl aminobenzoate
Ethyl 4-[bis(hydroxypropyl)] aminobenzoate
2-phenylbenzimidazole-5-sulfonic acid
Benzophenone-8
Benzophenone-6
Benzophenone-2
Benzophenone-1
Amyl dimethyl PABA
Benzophenone-4
Benzophenone-9

Antiperspirant Actives

Aluminum bromohydrate
Aluminum chlorohydrate
Aluminum dichlorohydrate
Aluminum sesquichlorohydrate
Aluminum chlorohydrex PG
Aluminum dichlorohydrex PG
Aluminum sesquichlorohydrex PG
Aluminum chlorohydrex PEG
Aluminum dichlorohydrex PEG
Aluminum sesquichlorohydrex PEG
Aluminum chloride Aluminum sulfate
Aluminum zirconium chlorohydrates
Aluminum zirconium trichlorohydrate
Aluminum zirconium tetrachlorohydrate
Aluminum zirconium pentachlorohydrate
Aluminum zirconium octachlorohydrate
Aluminum zirconium trichlorohydrex gly
Aluminum zirconium tetrachlorohydrex gly
Aluminum zirconium pentachlorohydrex gly
Aluminum zirconium octachlorohydrex gly
Buffered aluminum sulfate
Potassium alum
Sodium aluminum chlorohydroxy lactate In one preferred embodiment of the invention the core composition is used to make a clear moisturizing cream containing about 8-20% cetyl dimethicone copolyol, 10-35% cyclomethicone, 20-40% water, and about 8-25% of one or more inorganic salts. The cream may optionally contain a variety of ingredients as mentioned previously.

The preferred moisturizing creams of the invention are set forth in Example 1, wherein the silicone is cyclomethicone, the alcohol is isopropyl alcohol or SD-40 alcohol and the salts are one or more of magnesium chloride, magnesium sulfate, sodium thiosulfate or aluminum chloride. The high salt concentration of the core composition enables the addition of effective quantities of the humectant urea, which is a most desireable component of creams due to its hydrating effects. Preferably one or more of urea or propylene glycol is used for this purpose. The core composition additionally containing about 1-20% urea and/or about 1-15% propylane glycol provides an excellent mositurizing cream. Additional ingredients such as fragrances, may be added and the final pH of the composition may be adjusted with citric acid if desired. Various embodiments of the clear moisturizing composition of the invention are set forth in Example 1.

The core composition is also ideally suited for the manufacture of a clear antiperspirant composition. A particular advantage of the invention is the formulation of a clear, high viscosity antiperspirant cream using the most effective anti-perspirant active available and at the highest concentration allowed by law which is 20% of aluminum zirconium tetrachlorohydrex gly. The invention, however, is not limited to the use of aluminum zirconium tetrachlorohydrex gly since the more economical but slightly less effective aluminum chlorohydrate can be used. Another advantage of the invention is that urea may be added to the aluminum zirconium complex which further reduces, prevents and heals skin irritation in the high viscosity cream. The preferred range of core components when the core is used as the basis for an antiperspirant is also about 20-40% water, 8-20% cetyl dimethicone copolyol, 10-35% cyclomethicone and about 8-25% of one or more salts. The composition may additionally contain one or more of the additional ingredients mentioned previously and in particular humectants, solvents, emulsifiers, thickeners or masking agents are desireable. In the anti-perspirant composition the humectant may be urea, propylene glycol or both. The salts may be inorganic salts such as one or more of sodium chloride, sodium thiosulfate, alone or in conjunction with antiperspirant actives such as aluminum zirconium tetrachlorohydrex gly or aluminum chlorohydrate. A variety of solvents are desireable particulaly SD-40 alcohol, isopropyl alcohol and other similar alcohols. Preferably the co-emulsifier is methoxy PEG-22 dodecylcopolymer or oleic acid derivatives included therein such as sorbitan oleate or glycyrrhizic acid or its derivatives. A masking agent may be desireable to mask any medicinal odors. Ethylene brassylate, for example, is suitable for this use.

The antiperspirant composition preferably contains a humectant. One or more of urea or propylene glycol is suitable and the preferred ranges are 1-20% urea and-/or 1-15% propylene glycol. Any of the forementioned antiperspirant actives are suitable either as the salt component along or in conjunction with other organic or inorganic salts. For example, one or more of aluminum zirconium tetrachlorohydrex gly, aluminum chlorohydrate, or magnesium chloride may be used. Optional additives such as co-emulsifers, thickeners, masking agents, and so on, may be desired. The co-emulsifers glycyrrhizic acid, Elfacos E 200, sorbitol, or PEG-30 Glyceryl monoacetate were used in the invention along with ethylene brassylate as a masking agent.

In one further preferred embodiment of the invention the core composition is used to make a clear moisturizing sunscreen composition. The sunscreen composition contains the same component ranges of the clear moisturizing composition and additionally contains a humectant such as urea and/or propylene glycol and a U.V. absorber. Generally preferred are one or more of the humectants urea or propylene glycol in the range of 1-20% and 1-15% respectively. Any one or more of a U.V. absorber of Category I or Category II is suitable, for example 1.4-8% of octyl dimethyl PABA.

The invention will be further described in connection with the following examples which are set forth for the purposes of illustration only.

EXAMPLE 1

Clear moisturizing compositions were prepared as follows:

| Ingredient | Specimen No. (%) | | | | |
|---|---|---|---|---|---|
| | 60/11 | 60/12 | 51/3 | 89/11 | 92/1 |
| Urea | 13.0 | 13.5 | 14.0 | 12.0 | 14.0 |
| Abil B 9806/9808 | 10.0 | 10.0 | 11.0 | 12.0 | 11.0 |
| Cyclomethicone | 25.0 | 25.0 | 26.0 | 20.0 | 26.0 |
| Magnesium Sulfate | 13.0 | 5.0 | 13.0 | 11.0 | 13.0 |
| Water | 22.9 | 26.4 | 24.0 | 24.0 | 24.5 |
| Propylene glycol | 3.0 | 3.0 | — | 8.0 | — |
| Magnesium chloride | 2.0 | 2.0 | — | — | — |
| Alcohol SD-40 | 11.0 | 11.0 | 11.0 | 10.0 | 11.0 |
| Citric acid | 0.1 | 0.1 | — | — | — |
| Sodium thiosulfate | — | 5.0 | — | — | — |
| Aluminum chloride | — | — | 0.5 | 1.0 | 0.5 |
| Octyl dimethyl PABA | — | — | — | 2.0 | — |

EXAMPLE 2

Preparation of Antiperspirant

| Ingredient | Specimen No. (%) | | | | | |
|---|---|---|---|---|---|---|
| | 87/5 | 87/6 | 16/7 | 23/6 | 89/10 | 87/4 |
| Water | 22.5 | 35.0 | 20.0 | 25.0 | 22.0 | 25.0 |
| Urea | 2.5 | 3.0 | — | — | 2.0 | 5.0 |
| Propylene glycol | 8.8 | 5.0 | 10.0 | 11.6 | 8.0 | — |
| Abil B 9806 | 16.0 | 10.0 | 20.0 | 15.0 | 16.0 | 12.0 |
| Cyclomethicone | 20.0 | 15.0 | 20.0 | 15.0 | 20.0 | 28.0 |
| SD-40 alcohol | 10.0 | — | 10.0 | 8.0 | 10.0 | 10.0 |
| Al/Zr tetrachlorohydrex gly | 20.0 | 20.0 | 20.0 | 20.0 | — | 20.0 |
| Elfacos E 200* | — | 5.0 | — | 5.0 | — | — |
| Glycyrrhizic acid | — | — | — | 0.4 | — | — |
| Aluminum chlorohydrate | — | — | — | — | 20.0 | — |
| Aluminum chloride | — | — | — | — | 2.0 | — |
| Ethylene brassylate | 0.2 | — | — | — | — | — |
| PEG-30 Glyceryl Monococoate | — | 2.0 | — | — | — | — |
| Sorbitol | — | 5.0 | — | — | — | — |

*methoxy PEG-22 dodecyl copolymer

I claim:

1. A clear water in oil microemulsion moisturizing cream composition comprising the following essential constituents:
   (a) 8-20% of an ingredient selected from the group consisting of a mixture having an HLB 4-6 of cetyl dimethicone copolyol, polyglyceryl-3 oleate, and hexyl laurate; a mixture having an HLB 4-6 of cetyl dimethicone copolyol, polyglyceryl-4-isostearate, and hexyl laurate; cetyl dimethicone copolyol of HLB 4-6; and a mixture having an HLB 4-6 of cetyl dimethicone copolyol and hexyl laurate
   (b) 20-40% water,
   (c) 10-35% of a silicone selected from the group consisting of a polydimethylsiloxane having molecular weight of about 500-26,000, a polymethyl hydrogen siloxane of molecular weight about 500-23,000, cyclomethicone, phenyl dimethicone, hexamethyldisiloxane, trimethylsiloxysilicate, and stearoxy trimethylsilane,
   (d) 5-15% of a $C_{1-6}$ organic alcohol selected from the group consisting of SD-40 alcohol and isopropyl alcohol,
   (e) 8-20% by weight of a salt selected from the group consisting of an organic salt and inorganic salt wherein the inorganic salt is sodium chloride, magnesium sulfate, aluminum zirconium tetrachlorohydrex gly, magnesium chloride, sodium thiosulfate, aluminum chloride, aluminum chlorohydrate, sodium acetate, sodium citrate, sodium phosphate, or calcium chloride or mixtures thereof, and the organic salt is sodium aluminum lactate, sodium butoxyethyoxy acetate, sodium caprylate, sodium citrate, sodium lactate, sodium dihydroxyglycinate, sodium gluconate, sodium glutamate, sodium hydroxymethane sulfonate, sodium oxalate, sodium phenate, sodium propionate, sodium saccharidine, sodium salicylate, sodium sarcosinate, sodium tolene sulfonate, magnesium aspartate, calcium propionate, calcium saccharine, calcium-D-saccharate, calcium thioglycolate, aluminum caprylate, aluminum citrate, aluminum diacetate, aluminum glycinate, aluminum lactate, aluminum methionate, aluminum phenosulfonate, potassium aspartate, potassium biphthalate, potassium bitartrate, potassium glycosulfate, potassium sorbate, potassium thioglycolate, potassium toluenesulfonate, potassium troclosene, magnesium lactate, or mixtures thereof,
   (f) 1-20% of a humectant selected from the group consisting of urea and propylene glycol.

2. The composition of claim 1 wherein the inorganic salt is sodium chloride, magnesium sulfate, aluminum zirconium tetrachlorohydrex gly, magnesium chloride, sodium thiosulfate, aluminum chloride, aluminum chlorohydrate, sodium acetate, sodium citrate, sodium phosphate, or calcium chloride.

3. The composition of claim 1 which is a clear moisturizing cream additionally containing one or more humectant.

4. The composition of claim 1 containing 1-15% propylene glycol.

* * * * *